United States Patent [19]

Siemer et al.

[11] 4,235,622

[45] Nov. 25, 1980

[54] REDUCTION OF ACID LEVEL IN POMEGRANATES

[75] Inventors: Sidney R. Siemer, Columbia, Md.; Richard S. Gordon, St. Louis, Mo.

[73] Assignee: W. R. Grace & Co., New York, N.Y.

[21] Appl. No.: 33,883

[22] Filed: Apr. 27, 1979

[51] Int. Cl.³ ...................... A01N 37/02; A01N 35/02
[52] U.S. Cl. ......................................... 71/113; 71/122
[58] Field of Search .................................. 71/113, 122

[56] References Cited

U.S. PATENT DOCUMENTS

| | | | |
|---|---|---|---|
| 3,870,503 | 3/1975 | Nickell | 71/113 |
| 3,994,715 | 11/1976 | Nickell | 71/122 |
| 4,033,755 | 7/1977 | Nickell | 71/113 |

OTHER PUBLICATIONS

Tung et al., "Effect of Soil Aliphatic Acids On Young Cane Growth", Taiwan Tang Yeh Shin Yeh So Yen Chin Hui Pao, No. 41 (1966), pp. 45-50, Chem, Abs., vol. 67 (1967), 89968a.

*Primary Examiner*—Catherine L. Mills
*Attorney, Agent, or Firm*—Phillip M. Pippenger

[57] ABSTRACT

Disclosed herein is a method of reducing the acid level in pomegranates by applying thereto vanillin or a carboxylic acid salt having from 3 to 5 carbon atoms. Pomegranates are customarily harvested when the acidity level is about 18½ percent and application of the compounds of the present invention give the grower a better means of controlling acidity level so that the fruit can be harvested in an orderly manner.

9 Claims, No Drawings

REDUCTION OF ACID LEVEL IN POMEGRANATES

BACKGROUND OF THE INVENTION

Pomegranates are customarily harvested at an acid level of about 18½ percent. The acid level is generally determined by expressing the seeds from the fruit, pureeing the seeds followed by titration of the juice with NaOH. This method is generally described in the publication by the California Department of Food and Agriculture entitled "Fruit and Vegetable Standardization," Title III, Article 37 (Register 75, No. 4, 1-25-75), section 1464.4.

In marketing pomegranates, the market demand is established early in the season. As other fruits come on the market, it is desirable to maintain the flow of pomegranates so that the market share of fruit does not decline, i.e., customers will switch to other fruits if pomegranates do not remain readily available. Accordingly, it is desirable to harvest the pomegranates in an orderly manner which is not entirely dependent upon the whims of nature. A major objective of the present invention is to enable pomegranates to be harvested on "schedule" so that a continuous supply is maintained in fresh fruit markets.

The use of ammonium isobutyrate (AIB) as a ripening agent for sugarcane is described in U.S. Pat. No. 4,033,755. Other relevant U.S. Pat. Nos. included 3,870,503 (sodium isobutyrate), 3,909,238 (polyethoxylated surfactants), and 3,994,715 (vanillin).

DESCRIPTION OF THE INVENTION

The invention is a method for reducing the acid level in pomegranates prior to harvest by applying to the fruit a compound selected from the group consisting of vanillin (i.e. 4-hydroxy-3-methoxybenzaldehyde) or a carboxylic acid salt containing 3 to 5 carbon atoms. The carboxylic acid salt should be water soluble or at least water dispersible through the use of a surfactant. Suitable salts include AIB, calcium isobutyrate, magnesium isobutyrate, sodium isobutyrate, potassium isobutyrate, ammonium butyrate, sodium butyrate, ammonium propionate, sodium propionate, calcium propionate, magnesium propionate and potassium propionate. Generally, the acid cation is sodium, potassium, calcium, magnesium or ammonium.

In practicing the invention it is important to realize that acid values tend to fluctuate from season to season and from plant to plant. Therefore, application of the compounds of the invention will not always result in the same reduction in acidity in the same amount of time. Generally, the compounds should be applied at from 4 to 40 days prior to the intended harvest time. In some pomegranates it may be possible to lower the acidity level to 18½ percent by application as little as 4 days prior to harvest, whereas the majority of cases, application at from 7 to 28 days prior to harvest is preferable, i.e., the acid level is most likely to be 18½ percent or less at the time it is desired to harvest the fruit.

The compounds are applied at a rate of from 1 to 50 pounds per acre and 2 to 5 pounds is optimal. Above 5 pounds per acre the increase in effect is nominal, especially in view of the increase in cost of the compound applied.

The compounds are employed in the form of aqueous solutions or dispersions. Generally, where the application device is a spray gun, boom or other device where the solution is expressed through a narrow orifice by pressure, the application rate is 50 to 200 gallons of solution per acre. Where the application is by means of an air sprayer, i.e., the solution is entrained in a fast moving air stream, more concentrated solutions are employed and about 5 to 50 gallons per acre can be used. Regardless of the amount of solution employed, the pounds of active ingredients applied per acre should be within the ranges described above.

In the aqueous solutions employed, it is generally advisable to use a surfactant to prevent the solution from forming globules and "rolling off" upon contact with the leaves of the plant. The surfactant level is generally from 0.1 to 15% by volume of the total formulation and 0.1 to 1½% is preferred. Suitable surfactants which can be employed include:

sorbitan monolaurate—undiluted
sorbitan monopalmitate—50% in $H_2O$
sorbitan monostearate—30% in $H_2O$
sorbitan monooleate—undiluted
sorbitan trioleate—undiluted
polyoxyethylene (20) sorbitan monolaurate—undiluted
polyoxyethylene (4) sorbitan monolaurate—undiluted
polyoxyethylene (20) sorbitan monopalmitate—undiluted
polyoxyethylene (20) sorbitan monostearate—undiluted
polyoxyethylene (4) sorbitan monostearate—60% in $H_2O$
polyoxyethylene (20) sorbitan tristearate—60% in $H_2O$
polyoxyethylene (20) sorbitan monooleate—undiluted
polyoxyethylene (5) sorbitan monooleate—undiluted
polyoxyethylene (20) sorbitan trioleate—undiluted
polyoxyethylene (2) cetyl ether 98 at 60% in $H_2O$ 100 at 20% in $H_2O$
polyoxyethylene (10) cetyl ether—60% in $H_2O$
polyoxyethylene (20) cetyl ether—60% in $H_2O$
polyoxyethylene (2) stearyl ether—60% in $H_2O$
polyoxyethylene (10) stearyl ether—60% in $H_2O$
polyoxyethylene (20) stearyl ether—60% in $H_2O$
polyoxyethylene (2) oleyl ether—undiluted
polyoxyethylene (10) oleyl ether—undiluted
polyoxyethylene (20) oleyl ether—undiluted The above materials are commonly available under trade names such as "Tween", "Span", "Brij", and "Carbowax". Other surfactants which reduce surface tension can also be employed.

EXAMPLE

AIB and vanillin were applied to pomegranate trees at the rate of 1, 2 and 4 pounds of compound per acre. In applying the compounds, solutions were prepared by dispersing the required amount of the compound in water. For an application level of 1 pound/acre, 1 pound of compound is used for every 200 gallons of water. The amount is doubled for an application rate of 2 pounds/acre and 4 pounds per 200 gallons of water is employed for an application rate of 4 pounds/acre. Tween 20 (polyoxyethylene (20) sorbitan monolaurate) was employed as the surfactant. For AIB, the AIB/surfactant weight ratio was 2:1. For vanillin, the vanillin/surfactant weight ratio was 20:1.

In California where the tests of this example were performed, the average number of pomegranate trees per acre is about 100. Therefore, the average amount of solution applied to each tree is about 2 gallons. The solutions were applied using a $CO_2$ hand sprayer. The rate of application, time prior to harvest, and results obtained are set forth in the following Table. Each number in the Table represents the test results from a single tree. For each tree the results were obtained by taking four pomegranates, one from each "quadrant" at a level of about 8 feet from the ground. The seeds from each pomegranate were expressed and pureed and the acid level for each fruit was determined by NaOH titration as described above.

TABLE

| Treatment | Rate lbs AI/Acre | Variety and Days Post-Treatment | | |
| --- | --- | --- | --- | --- |
| | | Wonderful | Ruby Red | |
| | | 5 days | 5 days | 10 days |
| Untreated Control | — | 20.6% | 25.9% | 24.6% |
| AIB | 1 | 21.4 | 25.5 | 16.7 |
| | 2 | 17.2 | 24.5 | 19.5 |
| | 4 | 16.0 | 19.8 | 17.4 |
| Vanillin | 1 | 17.3 | 21.6 | 22.4 |
| | 2 | 16.8 | 21.5 | 16.9 |
| | 4 | 14.8 | 19.7 | 17.2 |

As indicated above, pomegranates are customarily harvested at an acidity level of $18\frac{1}{2}$ percent. For the "Wonderful" variety, the data in the Table shows that treatment levels of 2 and 4 pounds of AIB/acre would have allowed fruit to be harvested about 5 days after treatment. The untreated control, however, was still substantially above the $18\frac{1}{2}$ percent threshold as was also the 1 pound rate for AIB. Vanillin at all rates would have allowed fruit to be marketed 5 days after treatment.

Treatment of the Ruby Red variety with AIB showed that more time is required for acid reduction than for the variety Wonderful. The anomaly of the 2 pound/acre test being less effective than the 1 pound/acre rate is perhaps due to too small a sample size. The 4 pound treatment level would have allowed fruit to be marketed 10 days after application.

Like the AIB treatment, the vanillin application to the Ruby Red variety would not have allowed fruit to be harvested 5 days after application. At 10 days after application, the 1 pound rate was still not exerting sufficient effect on the Ruby Red variety. The 2 and 4 pound application rates would have allowed harvest after 10 days.

What is claimed is:

1. A method for decreasing the acidity in pomegranates having an acidity in excess of $18\frac{1}{2}$ percent, comprising applying to the leaves of the pomegranate plant, a compound selected from the group consisting of vanillin and carboxylic acid salts containing from 3 to 5 carbon atoms.

2. A method as in claim 1 wherein the compound is vanillin.

3. A method as in claim 1 wherein the compound is a carboxylic acid salt.

4. A method as in claim 3 wherein a salt of propionic acid is employed.

5. A method as in claim 3 wherein a salt of butyric acid is employed.

6. A method as in claim 3 wherein a salt of isobutyric acid is employed.

7. A method as in claim 3 wherein the carboxylic acid salt is ammonium isobutyrate.

8. A method as in claim 1 wherein the compound is applied in aqueous solution in combination with a surfactant.

9. A method as in claim 1 wherein the compound is applied to reduce the acidity level to $18\frac{1}{2}$ percent prior to harvest.

* * * * *